US006156783A

United States Patent [19]
Gaster

[11] Patent Number: 6,156,783
[45] Date of Patent: Dec. 5, 2000

[54] SPIROAZABICYCLIC COMPOUNDS, PROCESSES FOR THEIR PREPARATION, AND THEIR PHARMACEUTICAL USE

[75] Inventor: Laramie Mary Gaster, Bishop's Stortford, United Kingdom

[73] Assignee: SmithKline Beecham p.l.c., Brentford, United Kingdom

[21] Appl. No.: 09/180,066

[22] PCT Filed: Apr. 30, 1996

[86] PCT No.: PCT/EP97/01899

§ 371 Date: Oct. 30, 1998

§ 102(e) Date: Oct. 30, 1998

[87] PCT Pub. No.: WO97/41125

PCT Pub. Date: Nov. 6, 1997

[30] Foreign Application Priority Data

Apr. 30, 1996 [GB] United Kingdom .................... 9608828
Apr. 30, 1996 [GB] United Kingdom .................... 9608850
Apr. 30, 1996 [GB] United Kingdom .................... 9608851
Apr. 30, 1996 [GB] United Kingdom .................... 9608852

[51] Int. Cl.$^7$ .................... A61K 31/40; C07D 209/54

[52] U.S. Cl. ............................................. 514/409; 548/411
[58] Field of Search ................................ 548/357.5, 411; 514/409

[56] References Cited

FOREIGN PATENT DOCUMENTS

| 0 004 952 A1 | 4/1979 | European Pat. Off. . |
| 0 431 943 A2 | 12/1990 | European Pat. Off. . |
| 0 533 266 A1 | 9/1992 | European Pat. Off. . |
| 0 533 267 A1 | 9/1992 | European Pat. Off. . |
| 0 533 268 A1 | 9/1992 | European Pat. Off. . |
| 0 564 358 A1 | 4/1993 | European Pat. Off. . |
| 0 635 497 A2 | 7/1994 | European Pat. Off. . |
| WO 96/11934 | 4/1996 | WIPO . |
| WO 96/19477 | 6/1996 | WIPO . |

*Primary Examiner*—Deborah C. Lambkin
*Attorney, Agent, or Firm*—James M. Kanagy; Charles M. Kinzig

[57] ABSTRACT

Novel azabicyclic derivatives, processes for their preparation, pharmaceutical compositions containing them and their use as medicaments are disclosed.

11 Claims, No Drawings

SPIROAZABICYCLIC COMPOUNDS, PROCESSES FOR THEIR PREPARATION, AND THEIR PHARMACEUTICAL USE

This application is a 371 of PCT/EP97/018,899 Apr. 30, 1996.

The present invention relates to novel azabicyclic derivatives, processes for their preparation, and pharmaceutical compositions containing them.

EPA 0 533 266/7/8 disclose a series of benzanilide derivatives which are said to possess $5HT_{1D}$ receptor antagonist activity. PCT/EP/95/04889 discloses further $5HT_{1D}$ receptor antagonists having a spiropiperidine structure. These compounds are said to be of use in the treatment of various CNS disorders. The $5HT_{1D\beta}$ receptor has now been reclassified as the $5HT_{1B}$ receptor (P. R. Hartig et al., Trends in Pharmacological Science, 1996, 17, 103–105).

A structurally distinct class of compounds have now been discovered and have been found to exhibit $5HT_{1B}$ receptor antagonist activity. In a first aspect, the present invention therefore provides a compound of formula (I) or a salt or N-oxide thereof:

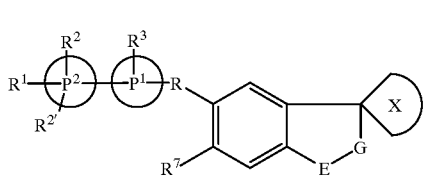

(I)

in which

P$^1$ and P$^2$ are independently phenyl, bicyclic aryl, a 5 to 7-membered heterocyclic ring containing 1 to 4 heteroatoms selected from oxygen, nitrogen or sulphur, or a bicyclic heterocyclic ring containing one to three heteroatoms selected from oxygen, nitrogen or sulphur;

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, N=CNR$^9$NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, or NR$^{12}$COR$^{13}$ where R$^9$, R$^{10}$ and R$^{11}$ are independently hydrogen or C$_{1-6}$alkyl, p is 1 to 4, R$^{12}$ is hydrogen, C$_{1-6}$alkyl or together with R$^{2'}$ forms a group (CH$_2$)$_k$ where k is 2, 3 or 4 or R$^{13}$ is hydrogen, C$_{1-6}$alkyl or optionally substituted aryl; or R$^1$ is an optionally substituted 5 to 7-membered heterocyclic ring containing 1 to 4 heteroatoms selected from oxygen, nitrogen or sulphur;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl, or R$^2$ and R$^3$ together form a group —(CH$_2$)$_r$—R$^{14}$—(CH$_2$)$_s$— where R$^{14}$ is O, S, CH$_2$ or NR$^{15}$ where R$^{15}$ is hydrogen or C$_{1-6}$alkyl and r and s are independently 0, 1 or 2;

R is a group —DR$^6$—C(=B)— or —C(=B)DR$^6$—;

B is oxygen or sulphur;

D is nitrogen or a CH group;

R$^6$ is hydrogen or C$_{1-6}$alkyl and R$^7$ is hydrogen, C$_{1-6}$alkyl, C$_{1-6}$alkoxy or halogen or R$^6$ together with R$^7$ forms a group —A— where A is (CR$^{16}$R$^{17}$)$_t$ where t is 2, 3 or 4 and R$^{16}$ and R$^{17}$ are independently hydrogen or C$_{1-6}$alkyl or A is (CR$^{16}$R$^{17}$)$_u$—J where u is 0, 1, 2 or 3 and J is oxygen, sulphur, CR$^{16}$=CR$^{17}$, CR$^{16}$=N, =CR$^{16}$O, =CR$^{16}$S or =CR$^{16}$—NR$^{17}$;

E is oxygen, CR$^{18}$R$^{19}$ and NR$^{20}$ where R$^{18}$, R$^{19}$ or R$^{20}$ are independently hydrogen or C$_{1-6}$alkyl or E is S(O)$_v$ where v is 0, 1 or 2;

G is C=O or CR$^{21}$R$^{22}$ where R$^{21}$ and R$^{22}$ are independently hydrogen or C$_{1-6}$alkyl; and X is an optionally substituted 7,6, 7,5, 6,6 or 6,5 bicyclic ring containing a nitrogen atom and optionally a further heteroatom selected from oxygen, nitrogen or sulphur.

C$_{1-6}$alkyl groups, whether alone or as part of another group, may be straight chain or branched. As used herein the term aryl includes phenyl and naphthyl. Heteroaryl groups include thienyl, furyl, pyridyl, pyrimidyl and pyrazinyl groups. Optional substituents for aryl and heteroaryl groups include those groups listed above for R$^2$/R$^3$.

Suitably P$^1$ and P$^2$ are independently selected from phenyl, bicyclic aryl, a 5- to 7-membered heterocyclic ring containing 1 to 4 heteroatoms selected from oxygen, nitrogen or sulphur, or a bicyclic heterocyclic ring containing one to three heteroatoms selected from oxygen, nitrogen or sulphur. Examples of bicyclic aryl groups include naphthyl. Examples of bicyclic heterocyclic rings include quinoline, isoquinoline, benzofuran and benzothiophene. Examples of suitable monocyclic heterocyclic rings include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl. Preferably P$^1$ and P$^2$ are both phenyl. The P$^1$ and P$^2$ groups can be attached to the remainder of the molecule at any suitable points.

Suitable R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, N=CNR$^9$NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, or NR$^{12}$COR$^{13}$ where R$^9$, R$^{10}$ and R$^{11}$ are independently hydrogen or C$_{1-6}$alkyl, p is 1 to 4, R$^{12}$ is hydrogen, C$_{1-6}$alkyl or together with R$^{2'}$ forms a group (CH$_2$)$_k$ where k is 2, 3 or 4 or R$^{13}$ is hydrogen, C$_{1-6}$alkyl or optionally substituted aryl; or R$^1$ is an optionally substituted 5 to 7-membered heterocyclic ring containing 1 to 4 heteroatoms selected from oxygen, nitrogen or sulphur.

When R$^1$ is a 5 to 7-membered heterocyclic ring containing 1 to 3 heteroatoms selected from oxygen, nitrogen or sulphur suitable heterocyclic rings include thienyl, furyl, pyrrolyl, triazolyl, diazolyl, imidazolyl, oxazolyl, thiazolyl, oxadiazolyl, isothiazolyl, isoxazolyl, thiadiazolyl, pyridyl, pyrimidyl and pyrazinyl. Saturated and partially saturated rings are also within the scope of the invention, in particular rings including an oxo or thioxo moiety such as lactams and thiolactams. The heterocyclic rings can be linked to the remainder of the molecule via a carbon atom or, when present, a nitrogen atom. Suitable substituents for these rings include R$^2$ and R$^3$ groups as defined above. Preferably R$^1$ is optionally substituted 2-oxo-1-pyrrolidinyl group.

Suitably $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkylO$C_{1-6}$alkyl, acyl, aryl, acyloxy, hydroxy, nitro, trifluoromethyl, cyano, $CO_2R^9$, $CONR^{10}R^{11}$, $NR^{10}R^{11}$ where $R^9$, $R^{10}$ and $R^{11}$ are independently hydrogen or $C_{1-6}$alkyl, or $R^2$ and $R^3$ together form a group —$(CH_2)_r$—$R^{14}$—$(CH_2)_s$— where $R^{14}$ is O, S, $CH_2$ or $NR^{15}$ where $R^{15}$ is hydrogen or $C_{1-6}$alkyl and r and s are independently 0, 1 or 2.

Preferably $R^2$ is $C_{1-6}$alkyl. Preferably the $R^2$ groups is ortho with respect to the linkage between the $P^1$ and $P_2$ rings. Most preferably $R^2$ is methyl and $R^3$ is hydrogen.

Suitably R is a group —$DR^6$—C(=B)— or —C(=B) $DR^6$—, preferably R is —C(=B)$DR^6$—.

Suitably B is oxygen or sulphur. Preferably B is oxygen.

Suitably D is nitrogen or a CH group. Preferably D is nitrogen.

Suitably $R^6$ is hydrogen or $C_{1-6}$alkyl and $R^7$ is hydrogen, $C_{1-6}$alkyl, $C_{1-6}$alkoxy or halogen or $R^6$ together with $R^7$ forms a group —A— where A is $(CR^{16}R^{17})_t$ where t is 2, 3 or 4 and $R^{16}$ and $R^{17}$ are independently hydrogen or $C_{1-6}$alkyl or A is $(CR^{16}R^{17})_u$—J where u is 0, 1, 2 or 3 and J is oxygen, sulphur, $CR^{16}$=$CR^{17}$, $CR^{16}$=N, =$CR^{16}$O, =$CR^{16}$S or =$CR^{16}$—$NR^{17}$. Preferably $R^6$ together with $R^7$ forms a group —A— where A is $(CR^{16}R^{17})_t$ where t is 2 and $R^{16}$ and $R^{17}$ are both hydrogen.

Suitably E is oxygen, $CR^{18}R^{19}$ or $NR^{20}$ where $R^{18}$, $R^{19}$ and $R^{20}$ are independently hydrogen or $C_{1-6}$alkyl or E is $S(O)_v$ where v is 0, 1 or 2. Preferably E is oxygen.

Suitably G is C=O or $CR^{21}R^{22}$ where $R^{21}$ and $R^{22}$ are independently hydrogen or $C_{1-6}$alkyl. Preferably G is $CH_2$.

Suitably X is a 7,6, 7,5, 6,6 or 6,5 bicyclic ring containing a nitrogen atom and optionally a further heteroatom selected from oxygen, nitrogen or sulphur. Examples of such groups include tropane, isotropane, quinuclidine, isoquinuclidine, granatane, oxa-granatane, thia-granatane, aza-granatane, quinolizidine, indolizidine, 1-azabicyclo[3.2.1]octane, 1-azabicyclo[3.3.1]nonane, iso-granatane, oxaiso-granatane, and thiaisogranatane rings. It will be appreciated that the group X is attached to the rest of the molecule by a spiro-linkage. The 5, 6 or 7-membered rings of the group X can form the spiro-linkage. Optional substituents for such ring systems, which can be present on carbon and nitrogen atoms, include $C_{1-6}$alkyl such as methyl. More than one substituent can be present. Preferably X is indolizidine, 1-azabicyclo[3.3.1]nonane or tropane.

Preferred compounds of the invention include:

5-[2'-Methyl-4'-(2-oxo-1-pyrrolidinyl)biphenyl-4-carbonyl]-2,3,6,7-tetrahydrospiro[furo[2,3-f]indole-3,7'-indolizidine], 5-[2'-Methyl-4'-(2-oxopyrrolidin-1-yl)biphenyl-4-carbonyl]-2,3,6,7-tetrahydrospiro[furo[2,3-f]indole-3,4'-(1-azabicyclo[3.3.1]nonane)], 5-[2'-Methyl-4'-(2-oxopyrrolidin-1-yl)biphenyl-4-carbonyl]-8'-methyl-2,3,6,7-tetrahydrospiro[furo[2,3-f]indole-3,3'-tropane], or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises:

(a) for compounds of formula (I) where D is nitrogen, B is oxygen reaction of a compound of formula (II):

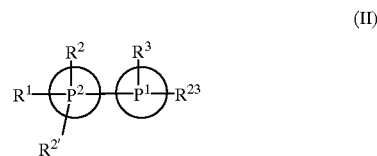

(II)

in which $P^1$, $P^2$, $R^1$, $R^2$, $R^{2'}$ and $R^3$ are groups as defined in formula (I) or protected derivatives thereof with a compound of formula (III):

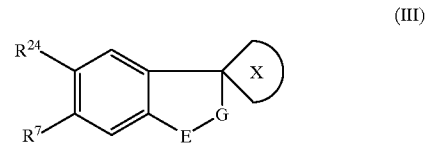

(III)

wherein $R^7$, E, G and X are groups as defined in formula (I) or protected derivatives thereof, and $R^{23}$ and $R^{24}$ contain the appropriate functional group(s) necessary to form the R moiety, and optionally thereafter in any order:

removing any protecting groups,
converting a compound of formula (I) into another compound of formula (I),
forming a pharmaceutically acceptable salt.

Suitably one of $R^{23}$ or $R^{24}$ is an activated carboxylic acid derivative, such as an acyl halide or acid anhydride, and the other is an amine group. Activated compounds of formulae (II) or (III) can also be prepared by reaction of the corresponding carboxylic acid with a coupling reagent such as carbonyldiimidazole, dicyclohexylcarbodiimide or diphenylphosphorylazide. Preferably $R^{23}$ or $R^{24}$ is a group COL where L is halo, particularly chloro.

A compound of formulae (II) and (III) are typically reacted together in an inert organic solvent such as DMF, THF or dichloromethane at ambient or elevated temperature in the presence of a base such as triethylamine, pyridine or alkali metal hydroxide. Compounds of formulae (II) and (III) can be prepared from the corresponding carboxylic acids using standard procedures. For example acid chlorides can be prepared by reaction with phosphorous pentachloride, oxalyl chloride or thionyl chloride. Acid anhydrides can be prepared by reaction with a suitable acid anhydride, for example trifluoroacetic anhydride.

Alternatively L is an ester forming group such that the resulting esters of formula (III) can be reacted with compounds of formula (II) in the presence of an organo-aluminium reagent such as trimethylaluminium. Such a reaction is typically carried out in the presence of an inert solvent such as toluene.

Intermediate compounds of formula (II) and (III) can be prepared using standard procedures known in the art. Certain intermediate compounds of formula (II) and (III) are novel and form a further aspect of the invention.

It will be appreciated to those skilled in the art that it may be necessary to protect certain reactive substituents during some of the above procedures. Standard protection and deprotection techniques can be used such as those described in Greene, T. W., 'Protective groups in organic synthesis', New York, Wiley (1981). For example, primary amines can be protected as phthalimide, benzyl, benzyloxycarbonyl or trityl derivatives.

Carboxylic acid groups can be protected as esters. Aldehyde or ketone groups can be protected as acetals, ketals, thioacetals or thioketals. Deprotection is achieved using standard conditions.

$5HT_{1B}$ receptor antagonists, and in particular the compounds of the present invention, are expected to be of use in the treatment of CNS disorders such as mood disorders, including depression, seasonal affective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include motor disorders such as Parkinson's disease, dementia in Parkinson's disease, neuroleptic-induced Parkinsonism and tardive dyskinesias, as well as other psychiatric disorders.

$5HT_{1B}$ receptor antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction and hypothermia.

Therefore, the present invention provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following examples illustrate the invention.

DESCRIPTION 1

Ethyl 1,2,3,5,6,8a-hexahydroindolizine-7-carboxylate

The procedure of *Chem. Pharm. Bull.*, 1980, 28, 2783 was followed. Chromatography of the crude product on silica, eluting with 0–10% methanol in dichloromethane, gave the title compound.

$^1$H NMR (200 MHz, CDCl$_3$) δ (ppm): 6.91 (d, 1H), 4.20 (q, 2H), 3.47 (m, 1H), 3.02 (m, 1H), 2.80 (m, 3H), 2.38 (m, 2H), 2.08 (m, 1H), 1.84 (m, 2H), 1.58 (m, 1H), 1.30 (t, 3H).

DESCRIPTION 2

1,2,3,5,6,8a-Hexahydroindolizine-7-methanol

Ethyl 1,2,3,5,6,8a-hexahydroindolizine-7-carboxylate (D1, 0.89 g, 4.6 mmol) was stirred under Ar in dry THF (50 ml) as lithium aluminium hydride (0.35 g, 9.2 mmol) was added portionwise. After 30 min, the reaction was worked up by successive addition of water (0.35 ml), 10% NaOH (0.35 ml) and water (1.05 ml). The solid was filtered off, and the filtrate was evaporated to yield the title compound (0.67 g, 97%) as a brown oil.

$^1$H NMR (250 MHz, CDCl$_3$) δ (ppm): 5.67 (s, 1H), 3.96 (s, 2H), 2.5–3.9 (m, 6H), 1.2–2.3 (m, 6H).

DESCRIPTION 3

1-Acetyl-6-bromo-5-[(1,2,3,5,6,8a-hexahydroindolizin-7-yl)methoxy]indoline

1-Acetyl-6-bromo-5-hydroxyindoline (*Tetrahedron*, 1973, 29(8), 1115) (1.24 g, 4.8 mmol), 1,2,3,5,6,8a-hexahydroindolizine-7-methanol (D2, 0.74 g, 4.8 mmol) and triphenylphosphine (1.27 g, 4.8 mmol) were stirred under Ar in dry THF (50 ml) as diethyl azodicarboxylate (0.76 ml, 4.8 mmol) was added dropwise. The mixture was stirred for 1 h, diluted with ethyl acetate, and extracted with dil. HCl. The extract was basified with potassium carbonate, and extracted with chloroform. This extract was dried (Na$_2$SO$_4$) and evaporated to give a dark oil. Further treatment of this oil as above with the phenol, triphenylphosphine and diethyl azodicarboxylate caused reaction to proceed further. Chromatography on silica, eluting with 0–20% methanol/dichloromethane, gave the title compound (0.25 g, 13%) as a brown gum.

$^1$H NMR (200 MHz, CDCl$_3$) δ (ppm): 8.40 (s, 1H), 6.73 (s, 1H), 5.82 (s, 1H), 4.41 (s, 2H), 4.03 (t, 2H), 3.12 (t, 2H), 2.6–3.3 (m, 5H), 2.18 (s, 3H), 1.2–2.5 (m, 6H).

DESCRIPTION 4

5-Acetyl-2,3,6,7-tetrahydrospiro[furo[2,3-f]indole-3,7'-indolizidine]

1-Acetyl-6-bromo-5-[(1,2,3,5,6,8a-hexahydroindolizin-7-yl)methoxy]indoline (D3) (0.118 g, 0.3 mmol) and α,α'-azoisobutyronitrile (0.04 g) were stirred at reflux under Ar in benzene (40 ml) as tributyltin hydride (0.24 ml, 0.9 mmol) was added dropwise in benzene (10 ml) over 10 min. The mixture was stirred at reflux for 6 h, cooled, and extracted with dil. HCl. The extract was basified with saturated K$_2$CO$_3$, and extracted with chloroform. The organic extract was dried (Na$_2$SO$_4$) and evaporated to give the title compound (0.073 g, 77%) as a brown gum. NMR showed a mixture of two isomers.

$^1$H NMR (250 MHz, CDCl$_3$) δ (ppm): 8.44 (s) and 8.02 (s) (1H), 6.57 (s) and 6.54 (s) (1H), 4.12 (s, 2H), 3.9–4.4 (m, 2H), 2.8–3.2 (m, 4H), 2.15 (s) and 2.11 (s) (3H), 1.0–2.7 (m, 11H).

DESCRIPTION 5

2,3,6,7-Tetrahydrospiro[furo[2,3f]indole-3,7'-indolizidine]

5-Acetyl-2,3,6,7-tetrahydrospiro[furo[2,3-f]indole-3,7'-indolizidine] (D4, 0.079 g, 0.25 mmol) was stirred at reflux in a mixture of ethanol (10 ml) and 5M HCl (20 ml) for 2.5 h. The mixture was concentrated to small volume, basified with 10% Na$_2$CO$_3$ and extracted with chloroform. The extract was dried (Na$_2$SO$_4$) and evaporated to give the title compound (0.058 g, 85%) as a brown gum. NMR showed 2 isomeric components.

$^1$H NMR (200 MHz, CDCl$_3$) δ (ppm): 6.79 (s), 6.57 (s), 6.53 (s) and 6.37 (s) (2H), 4.07 (s, 2H), 3.46 (m, 2H), 2.6–3.2 (m, 4H), 0.8–2.6 (m, 12H).

DESCRIPTION 6

4-Trifluoromethanesulphonyloxy-1-azabicyclo[3.3.1]non-3-ene

A stirred solution of diisopropylamine (1.7 ml, 0.012 mole) in dry THF (20 ml) at −65° C. under argon was treated with 1.6M n-butyllithium in hexane (6.87 ml, 0.011 mole) and kept for 20 minutes, then treated dropwise over 10 minutes with a solution of 1-azabicyclo[3.3.1]nonan-4-one (1.4 g, 0.10 mole) in THF (20 ml). The mixture was stirred at −70° C. for 1.25 h, then treated with a solution of N,N-bis(trifluoromethanesulphonyl) aniline (3.93 g, 0.011 mole) in THF (20 ml) and the reaction mixture allowed to warm to room temperature and stir for 20 h. The solution was concentrated in vacuo and the residue chromatographed on neutral alumina eluting initially with 1:1 ether/60–80 petrol and increasing polarity to neat ether, then neat ethyl acetate to afford the title compound as a yellow oil (2.5 g), contaminated with some aniline product.

$^1$H NMR (250 MHz, CDCl$_3$) δ (ppm): 6.00 (t, 1H), 3.80 (d, 1H), 3.26 (dd, 1H), 3.11 (d, 1H), 3.15–2.85 (m, 3H), 2.40 (br s, 1H), 1.95–1.60 (m, 3H), 1.57–1.34 (m, 1H).

DESCRIPTION 7

Methyl 1-azabicyclo[3.3.1]non-3-en-4-yl Carboxylate

A stirred solution of 4-trifluoromethanesulphonyloxy-1-azabicyclo[3.3.1]non-3-ene (D6, 2.5 g, ≦0.0092 mole) in methanol (15 ml) was treated with triethylamine (2.6 ml, 0.018 mole) and triphenylphosphine (135 mg, 0.52 mmole), then carbon monoxide was bubbled through the stirring solution for 5 minutes, before palladium (II) acetate (60 mg, 0.27 mmole) was added. The reaction flask was sealed under a carbon monoxide balloon and stirred at 25° C. for 20 h. The mixture was filtered through a pad of kieselguhr and the filtrate was concentrated in vacuo. The residue was treated with 2M HCl acid (30 ml) and ethyl acetate (30 ml), then shaken well and the acid layer isolated, basified with solid K$_2$CO$_3$ and extracted with chloroform. The extract was dried (Na$_2$SO$_4$) and concentrated in vacuo to afford the title compound as a yellow oil (0.99 g, 54%).

$^1$H NMR (200 MHz, CDCl$_3$) δ (ppm): 7.22 (t, 1H), 3.78 (dt, 1H), 3.74 (s, 3H), 3.25 (dd, 1H), 3.10–2.88 (m, 3H), 2.80 (br d, 1H), 2.64 (br s, 1H), 1.80–1.40 (m, 3H), 1.30–1.18 (m, 1H).

DESCRIPTION 8

1-Azabicyclo[3.3.1]non-3-en-4-methanol

The title compound was prepared from methyl 1-azabicyclo[3.3.1]non-3-en-4-yl carboxylate (D7) using a similar procedure to Description 2 as a pale yellow oil (100%).

$^1$H NMR (250 MHz, CDCl$_3$) δ (ppm): 5.89 (m, 1H), 4.02 (d, 2H), 3.68 (dt, 1H), 3.20–2.78 (m, 5H), 2.50–2.28 (m, 1H), 2.10 (br s, 1H), 1.80–1.54 (m, 3H), 1.35–1.18 (m, 1H).

DESCRIPTION 9

1-Acetyl-5-(1-azabicyclo[3.3.1]non-3-en-4-yl)methoxy-6-bromo-2,3-dihydro-1H-indole The title compound was prepared from 1-azabicyclo[3.3.1]non-3-en-4-methanol (D8) using a similar procedure to Description 3 as a brown oil (100%) contaminated with some DEAD product.

$^1$H NMR (250 MHz, CDCl$_3$) δ (ppm): 8.44 (s, 1H), 6.75 (s, 1H), 6.08 (br s, 1H), 4.42 (s, 2H), 4.05 (t, 2H), 3.72 (br d, 1H), 3.15 (t, 2H), 3.20–2.80 (m, 5H), 2.25 (br s, 1H), 2.20 (s, 3H), 1.90–1.60 (m, 3H), 1.35–1.20 (m, 1H).

DESCRIPTION 10

5-Acetyl-2,3,6,7-tetrahydrospiro[furo[2,3-f]indole-3, 4'-(1-azabicyclo[3.3.1]nonane)]

The title compound was prepared from 1-acetyl-5-(1-azabicyclo[3.3.1]non-3-en-4-yl)methoxy-6-bromo-2,3-dihydro-1H-indole (D9) by a similar procedure to Description 4 using toluene as solvent. The two isomers (2:1 ratio) formed around the spirocyclic junction were separated by column chromatography on silica gel eluting with 0–15% methanol/chloroform.

Higher rf isomer (D10a, 15%)—$^1$H NMR (250 MHz, CDCl$_3$) δ (ppm): 7.95 (s, 1H), 6.67 (s, 1H), 4.20–3.95 (m, 4H), 3.58–3.32 (m, 2H), 3.30–2.75 (m, 6H), 2.47–2.33 (m, 1H), 2.25–1.80 (m, 4H), 2.19 (s, 3H), 1.68–1.42 (m, 2H).

8Lower rf isomer (D10b, 18%)—$^1$H NMR (250 MHz, CDCl$_3$) δ (ppm): 8.55 (s, 1H), 6.63 (s, 1H), 4.55 (d, 1H), 4.10–3.95 (m, 3H), 3.65–3.50 (m, 2H), 3.25–2.97 (m, 5H), 2.90 (br d, 1H), 2.20 (s, 3H), 2.15–1.65 (m, 5H), 1.55–1.38 (m, 2H).

DESCRIPTIONS 11a AND 11b 2,3,6,7-Tetrahydrospiro[furo[2,3-f]indole-3,4'-(1-azabicyclo[3.3.1]nonane)]

The two isomers of 5-acetyl-2,3,6,7-tetrahydrospiro[furo[2,3-f]indole-3,4'-(1-azabicyclo[3.3.1]nonane)] (D10a and D10b) were separately hydrolysed to give the two isomers of the title compound (D11a and D11b) following a similar procedure to Description 5.

Higher rf isomer (D11a, 83%)—$^1$H NMR (250 MHz, CDCl$_3$) δ (ppm): 6.67 (s, 1H), 6.36 (s, 1H), 4.18–3.93 (m, 2H), 3.70–2.75 (m, 10H), 2.45–2.30 (m, 1H), 2.25–1.80 (m, 4H), 1.70–1.40 (m, 2H).

Lower rf isomer (D11b, 88%)—$^1$H NMR (250 MHz, CDCl$_3$) δ (ppm): 6.90 (s, 1H), 6.65 (s, 1H), 4.50 (d, 1H), 3.94 (d, 1H), 3.65–3.40 (m, 4H), 3.25–2.80 (m, 7H), 2.15–1.30 (m, 7H).

DESCRIPTION 12

1-(4-Bromo-3-methylphenyl)pyrrolidin-2-one

A stirred solution of 4-bromo-3-methylaniline (50.3 g, 0.27 mole) and triethylamine (41.4 ml, 0.30 mole) in THF (250 ml) at 0° C. under argon was treated dropwise with 4-chlorobutyryl chloride (33.4 ml, 0.30 mole). The mixture was stirred for 1 hour at 0–5° C., then potassium t-butoxide (82.5 g, 0.74 mole) was added portionwise over 20 minutes, maintaining temperature below 25° C. The reaction mixture was stirred at 25° C. for a further 2.5 hrs, then treated with water (100 ml), followed after 0.25 hrs with 10% Na$_2$CO$_3$ solution and then extracted with ethyl acetate. The extract was washed with water, dil. HCl acid, then brine, dried (Na$_2$SO$_4$) and concentrated in vacuo to afford the title compound as a pale yellow solid (61.6 g, 89%).

$^1$H NMR (250 MHz, CDCl$_3$) δ (ppm): 7.54 (d, 1H), 7.48 (d, 1H), 7.30 (dd, 1H), 3.82 (t, 2H), 2.58 (t, 2H), 2.40 (s, 3H), 2.16 (quintet, 2H).

DESCRIPTION 13

2'-Methyl-4'-(2-oxopyrrolidin-1-yl)biphenyl-4-carboxylic Acid

A stirred mixture of 1-(4-bromo-3-methylphenyl)pyrrolidin-2-one (D12, 50 g, 0.20 mole) and 4-boronobenzoic acid (32 g, 0.20 mole) in DME (500 ml) was treated with a solution of sodium carbonate (94 g, 0.88 mole) in water (500 ml), then de-gassed by bubbling argon through for 0.25 hrs. Tetrakis (triphenylphosphine) palladium (0) (5 g) was added and the mixture heated under reflux for 22 hours, then allowed to cool and concentrated in vacuo to approx. 50% volume. The aqueous residue was diluted with water to approx. 1000 ml, washed with ethyl acetate, then acidified with conc. HCl acid. The precipitate was filtered off, washed with water, dried and recrystallised from ethanol to afford the title compound as a cream solid (30.3 g, 52%).

$^1$H NMR (250 MHz, d$^6$DMSO) δ (ppm): 8.01 (d, 2H), 7.67–7.58 (m, 2H), 7.49 (d, 2H), 7.25 (d, 1H), 3.86 (t, 2H), 2.52 (t, 2H), 2.25 (s, 3H), 2.09 (quintet, 2H).

DESCRIPTION 14

Methyl 2'-methyl-4'-(2-oxopyrrolidin-1-yl)biphenyl-4-carboxylate

The title compound was prepared from 2'-methyl-4'-(2-oxopyrrolidin-1-yl)biphenyl-4-carboxylic acid (D13) by stirring a DMF solution together with iodomethane and potassium carbonate for 3 hours, followed by dilution with water and extraction into ethyl acetate.

DESCRIPTION 15

1-Acetyl-6-bromo-5-[(8-methyltrop-2-en-3-yl)methoxy]indoline

Methyl 8-methyltrop-2-en-3-ylcarboxylate (*Acta. Chim. Acad. Sci. Hung.*, 1980, 104(3), 235–242) underwent lithium aluminium hydride reduction using the method of description 2 (quantiative), and the resulting 8-methyltrop-2-en-3-methanol was converted to the title compound by reaction with 1-acetyl-6-bromo-5-hydroxyindoline (*Tetrahedron*, 1973, 29, (8), 115) using the method of description 3 (53% over both steps), as an orange crystalline material.

$^1$H NMR (200 MHz, CDCl$_3$) δ (ppm): 8.41 (s, 1H), 6.7 (s, 1H), 5.92 (br s, 1H), 4.38 (s, 2H), 4.05 (t, 2H), 3.38–3.24 (m, 2H), 3.12 (t, 2H), 2.65–2.49 (m, 1H), 2.32 (s, 3H), 2.19 (s, 3H), 2.13–1.4 (m, 5H).

DESCRIPTION 16

5-Acetyl-8'-methyl-2,3,6,7-tetrahydrospiro[furo[2,3-f]indole-3,3'-tropane]

1-Acetyl-6-bromo-5-[(8-methyltrop-2-en-3-yl)methoxy]indoline (D15) was converted to a mixture of isomers of the title compound using the method of Description 4 (45%).

$^1$H NMR (200 MHz, CDCl$_3$) δ (ppm): 7.8 (s, 1H), 6.86 (s, 1H), 4.3 (m, 2H), 4.13 (s, 2H), 4.0 (t, 2H), 3.25 (s, 3H), 3.18–3.0 (m, 2H), 2.89 (t, 2H), 2.65–2.46 (m, 2H), 2.29–2.11 (m, 5H), 2.0–1.8 (m, 2H).

EXAMPLE 1

5-[2'-Methyl-4'-(2-oxo-1-pyrrolidinyl)biphenyl-4-carbonyl]-2,3,6,7-tetrahydrospiro[furo[2,3-f]indole-3,7'-indolizidine]

2'-Methyl-4'-(2-oxo-1-pyrrolidinyl)biphenyl-4-carboxylic acid (D13) (0.076 g, 0.25 mmol) was stirred under Ar in dichloromethane (5 ml). Oxalyl chloride (0.03 ml, 0.34 mmol) was added, followed by 1 drop of N,N- dimethylformamide. After stirring for 1 h, the mixture was evaporated to dryness, azeotroping with toluene. The residue was dissolved in dichloromethane (1 ml), and a mixture of 2,3,6,7-tetrahydrospiro[furo[2,3-f]indole-3,7'-indolizidine] isomers (D5, 0.056 g, 0.21 mmol) in dichloromethane (4 ml) and triethylamine (0.06 ml, 0.43 mmol) were added. After 2 h, the mixture was washed with 10% $Na_2CO_3$, dried ($Na_2SO_4$) and evaporated. The title compound (0.020 g, 16%) was purified by preparative layer chromatography (10% methanol/dichloromethane), followed by precipitation as the hydrochloride salt. NMR showed two isomeric components.

$^1$H NMR (HCl salt) (400 MHz, d$^6$DMSO) δ (ppm): 7.98 (b) and 7.82 (b) (1H), 7.6 (m, 4H), 7.42 (m, 2H), 7.23 (d, 1H), 6.78 (b) and 6.73 (s) (1H), 4.5 (m) and 4.26 (s) (2H), 4.04 (t, 2H), 3.86 (t, 2H), 3.56 (m, 1H), 3.15–3.4 (m, 2H), 3.0 (t, 2H), 2.9–3.15 (m, 2H), 2.50 (t, 2H), 2.27 (s, 3H), 2.10 (m, 2H), 1.6–2.3 (m, 8H).

EXAMPLES 2a AND 2b

5-[2'-Methyl-4'-(2-oxopyrrolidin-1-yl)biphenyl-4-carbonyl]-2,3,6,7-tetrahydrospiro[furo[2,3-f]indole-3,4'-(1-azabicyclo[3.3.1]nonane)]

The two isomers of the title compound were prepared separately from 2'-methyl-4'-(2-oxopyrrolidin-1-yl) biphenyl-4-carboxylic acid (D13) and the two separate isomers of 2,3,6,7-tetrahydrospiro[furo[2,3-f]indole-3,4'-(1-azabicyclo[3.3.1]nonane)] (D11a and D11b) using a similar procedure to Example 1. The hydrochloride salts were obtained as white solids.

Higher rf isomer (free base, E2a, 25%) (250 MHz, CDCl$_3$) δ (ppm): 8.00 (br s, 1H), 7.63–7.46 (m, 4H), 7.40 (d, 2H), 7.25 (d, 1H), 6.72 (s, 1H), 4.30–4.00 (m, 4H), 3.90 (t, 2H), 3.70–2.80 (m, 8H), 2.64 (t, 2H), 2.50–1.90 (m, 7H), 2.32 (s, 3H), 1.75–1.50 (m, 2H).

Lower rf isomer (free base, E2b, 16%) (250 MHz, CDCl$_3$) δ (ppm): 8.50 (br s, 1H), 7.66–7.30 (m, 7H), 6.69 (s, 1H), 4.65–4.50 (m, 1H), 4.30–3.90 (m, 3H), 3.90 (t, 2H), 3.77–3.50 (m, 1H), 3.30–2.50 (m, 7H), 2.65 (t, 2H), 2.30 (s, 3H), 2.30–1.40 (m, 9H).

EXAMPLE 3

5-[2'-Methyl-4'-(2-oxopyrrolidin-1-yl)biphenyl-4-carbonyl]-8'-methyl-2,3,6,7-tetrahydrospiro[furo[2,3-f]indole-3,3'-tropane]

The isomeric mixture of 5-acetyl-8'-methyl-2,3,6,7-tetrahydrospiro[furo[2,3-f]indole-3,3'-tropane] (D16) was hydrolysed to give an isomeric mixture of 8'-methyl-2,3,6,7-tetrahydrospiro[furo[2,3-f]indole-3,3'-tropane] using the method of Description 5 (73%). A solution of 8'-methyl-2,3,6,7-tetrahydrospiro[furo[2,3-f]indole-3,3'-tropane] isomers (50 mg; 0.185 mmol) in toluene (5 ml) was treated at room temperature under argon with trimethylaluminium (2M in toluene) (0.1 ml), followed 10 minutes later by a solution of methyl 2'-methyl-4'-(2-oxopyrrolidin-1-yl) biphenyl-4-carboxylate (D14) (57 mg; 0.185 mol) in toluene (5 ml) and the mixture heated to 80° C. under argon for 2 h, then overnight at room temperature. The cooled reaction mixture was evaporated in vacuo, and chromatographed on silica gel, eluting with methanol and chloroform, to give the title compound as a mixture of isomers (40 mg, 40%). The hydrochloride salt was prepared.

$^1$H NMR (HCl salt) (400 MHz, d$^6$DMSO) δ (ppm): 10.0 (br s, 1H), 8.35 (br) and 8.19 (br), (1H), 7.72–7.55 (m, 4H), 7.45 (m, 2H), 7.24 (d, 1H), 6.82 (s) and 6.75 (s) (1H), 4.7 (s) and 4.49 (d) (1H), 4.16–4.0 (m, 2H), 3.88 (t, 2H), 3.11–2.98 (m, 2H), 2.77–1.9 (m, 20H).

What is claimed is:

1. A compound of formula (I) or a salt or N-oxide thereof:

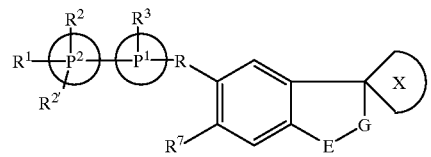

(I)

in which

P$^1$ and P$^2$ are independently phenyl, bicyclic aryl, a 5 to 7-membered heterocyclic ring containing 1 to 4 heteroatoms selected from oxygen, nitrogen or sulphur, or a bicyclic heterocyclic ring containing one to three heteroatoms selected from oxygen, nitrogen or sulphur;

R$^1$ is hydrogen, halogen, C$_{1-6}$alkyl, C$_{3-6}$cycloalkyl, COC$_{1-6}$alkyl, C$_{1-6}$alkoxy, hydroxy, hydroxyC$_{1-6}$alkyl, hydroxyC$_{1-6}$alkoxy, C$_{1-6}$alkoxyC$_{1-6}$alkoxy, acyl, nitro, trifluoromethyl, cyano, SR$^9$, SOR$^9$, SO$_2$R$^9$, SO$_2$NR$^{10}$R$^{11}$, CO$_2$R$^{10}$, NR$^{10}$SO$_2$R$^{11}$, CONR$^{10}$R$^{11}$, CO$_2$NR$^{10}$R$^{11}$, CONR$^{10}$(CH$_2$)$_p$CO$_2$R$^{11}$, (CH$_2$)$_p$NR$^{10}$R$^{11}$, (CH$_2$)$_p$CONR$^{10}$R$^{11}$, (CH$_2$)$_p$NR$^{10}$COR$^{11}$, (CH$_2$)$_p$CO$_2$C$_{1-6}$alkyl, CO$_2$(CH$_2$)$_p$OR$^{10}$, CONHNR$^{10}$R$^{11}$, NR$^{10}$R$^{11}$, N=CNR$^9$NR$^{10}$R$^{11}$, NR$^{10}$CO$_2$R$^{11}$, NR$^{10}$CO(CH$_2$)$_p$NR$^{10}$R$^{11}$, NR$^{10}$CONR$^{10}$R$^{11}$, CR$^{10}$=NOR$^{11}$, CNR$^{10}$=NOR$^{11}$, or NR$^{12}$COR$^{13}$ where R$^9$, R$^{10}$ and R$^{11}$ are independently hydrogen or C$_{1-6}$alkyl, p is 1 to 4, R$^{12}$ is hydrogen, C$_{1-6}$alkyl or together with R$^{2'}$ forms a group (CH$_2$)$_k$ where k is 2, 3 or 4 and R$^{13}$ is hydrogen, C$_{1-6}$alkyl or optionally substituted aryl; or R$^1$ is an optionally substituted 5 to 7-membered heterocyclic ring containing 1 to 4 heteroatoms selected from oxygen, nitrogen or sulphur;

R$^{2'}$ is hydrogen or together with R$^1$ forms a group (CH$_2$)$_k$ where k is 2, 3 or 4;

R$^2$ and R$^3$ are independently hydrogen, halogen, C$_{1-6}$alkyl, C$_{3-6}$cycloalkyl, C$_{3-6}$cycloalkenyl, C$_{1-6}$alkoxy, hydroxyC$_{1-6}$alkyl, C$_{1-6}$alkylOC$_{1-6}$alkyl, acyl, aryl, acyloxy, hydroxy, nitro, trifluoromethyl, cyano, CO$_2$R$^{10}$, CONR$^{10}$R$^{11}$, NR$^{10}$R$^{11}$ where R$^{10}$ and R$^{11}$ are independently hydrogen or C$_{1-6}$alkyl, or R$^2$ and R$^3$ together form a group —(CH$_2$)$_r$—R$^{14}$—(CH$_2$)$_s$— where R$^{14}$ is O, S, CH$_2$ or NR$^{15}$ where R$^{15}$ is hydrogen or C$_{1-6}$alkyl and r and s are independently 0, 1 or 2;

R is a group —DR$^6$—C(=B)— or —C(=B)DR$^6$—;

B is oxygen or sulphur;

D is nitrogen or a CH group;

R$^6$ is hydrogen or C$_{1-6}$alkyl and R$^7$ is hydrogen, C$_{1-6}$alkyl, C$_{1-6}$alkoxy or halogen or R$^6$ together with R$^7$ forms a group —A— where A is (CR$^{16}$R$^{17}$)$_t$ where t is 2, 3 or 4 and R$^{16}$ and R$^{17}$ are independently hydrogen or C$_{1-6}$alkyl or A is (CR$^{16}$R$^{17}$)$_u$—J where u is 0, 1, 2 or 3 and J is oxygen, sulphur, CR$^{16}$=CR$^{17}$, CR$^{16}$=N, =CR$^{16}$O, =CR$^{16}$S or =CR$^{16}$—NR$^{17}$;

E is oxygen, CR$^{18}$R$^{19}$ or NR$^{20}$ where R$^{18}$, R$^{19}$ or R$^{20}$ are independently hydrogen or C$_{1-6}$alkyl or E is S(O)$_v$ where v is 0, 1 or 2;

13

G is C=O or $CR^{21}R^{22}$ where $R^{21}$ and $R^{22}$ are independently hydrogen or $C_{1-6}$alkyl; and X is an optionally substituted indolazyl or indolizidinyl.

2. A compound according to claim 1 in which $P^1$ is phenyl.

3. A compound according to claim 1 in which $P^2$ is phenyl.

4. A compound according to claim 1 in which $R^2$ is $C_{1-6}$alkyl and $R^3$ is hydrogen.

5. A compound according to claim 1 in which R is —C(=B)DR$^6$—.

6. A compound according to claim 1 in which B is oxygen.

7. A compound according to claim 1 which is:

5-[2'-(2-oxo-1-pyrrolidinyl)biphenyl-4-carbonyl]-2,3,6,7-tetrahydrospiro[furo[2,3-f]indole-3,7'-indolizidine], or a pharmaceutically acceptable salt thereof.

8. A process for the preparation of a compound of formula (I)

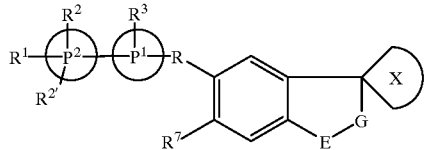

(I)

in which $P^1$ and $P^2$ are independently phenyl, bicyclic aryl, a 5 to 7-membered heterocyclic ring containing 1 to 4 heteroatoms selected from oxygen, nitrogen or sulphur, or a bicyclic heterocyclic ring containing one to three heteroatoms selected from oxygen, nitrogen or sulphur;

$R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}R^{11}$, $(CH_2)_pCONR^{10}R^{11}$, $(CH_2)_pNR^{10}COR^{11}$, $(CH_2)_pCO_2C_{1-6}$alkyl, $CO_2(CH_2)_pOR^{10}$, $CONHNR^{10}R^{11}$, $NR^{10}R^{11}$, $N=CNR^9NR^{10}R^{11}$, $NR^{10}CO_2R^{11}$, $NR^{10}CO(CH_2)_pNR^{10}R^{11}$, $NR^{10}CONR^{10}R^{11}$, $CR^{10}=NOR^{11}$, $CNR^{10}=NOR^{11}$, or $NR^{12}COR^{13}$ where $R^9$, $R^{10}$ and $R^{11}$ are independently hydrogen or $C_{1-6}$alkyl, p is 1 to 4, $R^{12}$ is hydrogen, $C_{1-6}$alkyl or together with $R^{2'}$ forms a group $(CH_2)_k$ where k is 2, 3 or 4 and $R^{13}$ is hydrogen, $C_{1-6}$alkyl or optionally substituted aryl; or $R^1$ is an optionally substituted 5 to 7-membered heterocyclic ring containing 1 to 4 heteroatoms selected from oxygen, nitrogen or sulphur;

$R^{2'}$ is hydrogen or together with $R^1$ forms a group $(CH_2)_k$ where k is 2, 3 or 4;

$R^2$ and $R^3$ are independently hydrogen, halogen, $C_{1-6}$alkyl, $C_{3-6}$cycloalkyl, $C_{3-6}$cycloalkenyl, $C_{1-6}$alkoxy, hydroxy$C_{1-6}$alkyl, $C_{1-6}$alkylOC$_{1-6}$alkyl, acyl, aryl, acyloxy, hydroxy, nitro, trifluoromethyl, cyano, $CO_2R^{10}$, $CONR^{10}R^{11}$, $NR^{10}R^{11}$ where $R^{10}$ and $R^{11}$ are independently hydrogen or $C_{1-6}$alkyl, or $R^2$ and $R^3$ together form a group —(CH$_2$)$_r$—R$^{14}$—(CH$_2$)$_s$— where $R^{14}$ is O, S, CH$_2$ or NR$^{15}$ where $R^{15}$ is hydrogen or $C_{1-6}$alkyl and r and s are independently 0, 1 or 2;

R is a group —DR$^6$—C(=B)— or —C(=B)DR$^6$—;

B is oxygen or sulphur;

14

D is nitrogen or a CH group;

$R^6$ is hydrogen or $C_{1-6}$alkyl and $R^7$ is hydrogen, $C_{1-6}$alkyl, $C_{1-6}$alkoxy or halogen or $R^6$ together with $R^7$ forms a group —A— where A is $(CR^{16}R^{17})_t$ where t is 2, 3 or 4 and $R^{16}$ and $R^{17}$ are independently hydrogen or $C_{1-6}$alkyl or A is $(CR^{16}R^{17})_u$—J where u is 0, 1, 2 or 3 and J is oxygen, sulphur, $CR^{16}$=$CR^{17}$, $CR^{16}$=N, =$CR^{16}$O, =$CR^{16}$S or =$CR^{16}$—NR$^{17}$;

E is oxygen, $CR^{18}R^{19}$ and $NR^{20}$ where $R^{18}$, $R^{19}$ or $R^{20}$ are independently hydrogen or $C_{1-6}$alkyl or E is S(O)$_v$ where v is 0, 1 or 2;

G is C=O or $CR^{21}R^{22}$ where $R^{21}$ and $R^{22}$ are independently hydrogen or $C_{1-6}$alkyl; and X is an optionally substituted indolazyl or indolizidinyl;

or a pharmaceutically salt thereof;

which comprises:

(a) for compounds of formula (I) where D is nitrogen and, B is oxygen reaction of a compound of formula (II):

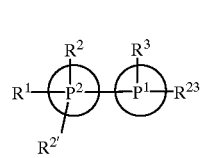

(II)

in which $P^1$, $P^2$, $R^1$, $R^2$, $R^{2'}$ and $R^3$ are groups as defined in formula (I) or protected derivatives thereof with a compound of formula (III):

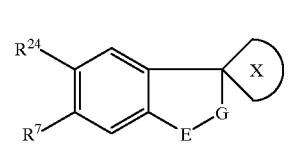

(III)

wherein $R^7$, E, G and X are groups as defined in formula (I) or protected derivatives thereof, and $R^{23}$ and $R^{24}$ where one of $R^{23}$ and $R^{24}$ is an acyl halide or acid anhydride group and the other is an amine group and optionally thereafter in any order, removing any protecting groups, or forming a pharmaceutically acceptable salt.

9. A method of antagonizing the 5HT$_{1B}$ receptor in a subject which comprises administering to the subject an effective amount of a compound of Formula (I), as defined in claim 1.

10. A method of treating depression, seasonal effective disorder, dysthymia, anxiety, panic disorder, agoraphobia, social phobia, obsessive compulsive disorder, post-traumatic stress disorder, dementia, age-associated memory impairment, anorexia nervosa, bulimia nervosa, Parkinson's disease, dementia in Parkinson's disease, neuroleptic-induced Parkinsonism, tardive dyskinesias which method involves administering to a patient in need thereof a therapeutically effective amount of a compound of Formula (I), as defined in claim 1.

11. A method of treating hyperprolactinaemia, vasospasm, hypertension and sexual dysfunction which method involves administering to a patient in need thereof a therapeutically effective amount of a compound of Formula (I), as defined in claim 1.

* * * * *